(12) United States Patent
Papadakos

(10) Patent No.: US 6,280,709 B1
(45) Date of Patent: Aug. 28, 2001

(54) PREPARATION OF SUN PROTECTION OIL

(76) Inventor: John Papadakos, 19 Antheon Street., 154 52 P.Psychiko, Athens (GR)

( * ) Notice: Subject to any disclaimer, the term of this patent is extended or adjusted under 35 U.S.C. 154(b) by 0 days.

(21) Appl. No.: 09/283,517

(22) Filed: Apr. 1, 1999

(30) Foreign Application Priority Data

Apr. 10, 1998 (GR) .............................................. 980100132

(51) Int. Cl.⁷ ...................................................... A61K 7/42

(52) U.S. Cl. .......................... 424/59; 424/401; 424/195.1

(58) Field of Search .................................. 424/59, 195.1, 424/401

(56) References Cited

PUBLICATIONS

Wenninger, et al., International Cosmetic Ingredient Dictionary and Handbook, Seventh Edition, vol. 2, pp. 897, 1200 and 1411, 1997.*

Wilkinson, et al., Harry's Cosmeticology, Seventh Edition, pp. 231–251, 1982.*

* cited by examiner

Primary Examiner—Michael A. Williamson
(74) Attorney, Agent, or Firm—Herbert Dubno; Jonathan Myers

(57) ABSTRACT

The sun protection oil of the invention is prepared with pure virgin olive oil as a basic constituent, in combination with an addition of vitamins E and A, has a U.V protection five (5) and axcept for its sun protection properties it is a skin treatment, as it retards aging of skill cells and maintains the skin youthfull and soft.

3 Claims, No Drawings

PREPARATION OF SUN PROTECTION OIL

FIELD OF THE INVENTION

The present invention relates to a sun protection oil, that is invented for the first time, produced and distributed in the market by me exclusively.

BACKGROUND OF THE INVENTION

As it is known there are distributed in the market numerous sun lotions and sun protection oils, the effectiveness of which vary according to their synthesis, however no one of them contains as basic ingredient olive oil, which olive oil possesses significant properties as regard to human skin.

Since ancient years, the olive oil is being used as a main factor of body hygiene, as with proper application its properties contribute to better blood circulation, make the skin more elastic, it is also disinfencant as it destroys certain picroorganisms, while at the same time restricts action of others and the most important is that it enriches the skin with various nutritive substances.

SUMMARY OF THE INVENTION

With the present invention is prepared a sun protection oil based on virgin oil, which with the properties it possesses in combination with a percentage of vitamin E—being lipid soluble and due to its antioxidizing action, retards aging of cells and comes from the seedling of cereals—as well as vitamin A—which comes from carrots and helps the skin to remain soft and not to become dry ), not only offers complete sun protection but at the same time is a skin treatment with the skin maintained youthful and soft.

More specifically, the sun protection oil of the invention contains pure virgin oil as a basic constituent to which a 3% of Vitamin E and a 3% of Vitamin A is added and said mixture is mixed properly. The resulting sun protection oil possesses a U.V protection five (5) and packed in bottles of various weight of content to meet consumers demands as regards contents.

What is claimed is:

1. A sun protective oil which provides protection at a level of 5 of the skin against ultraviolet radiation and retards aging of the skin and which consists of:

(a) 3% by weight Vitamin A;

(b) 3% by weight Vitamin E; and (c) balance pure virgin olive oil.

2. A method of protecting a patient from ultraviolet radiation which comprises the step of treating the skin of the patient with an effective amount of the sun protective oil defined in claim 1.

3. A method of retarding aging if the skin of a patient which comprises the step of treating the skin of the patient with an effective amount of the sun protective oil defined in claim 1.

* * * * *